(12) United States Patent
Hayward et al.

(10) Patent No.: US 7,691,444 B2
(45) Date of Patent: Apr. 6, 2010

(54) PRESERVATIVES FOR WOOD-BASED PRODUCTS

(75) Inventors: Peter James Hayward, New Plymouth (NZ); George William Mason, New Plymouth (NZ); Thomas Jaetsch, Köln (DE)

(73) Assignee: LANXESS Deutschland GmbH, Leverkusen (DE)

( * ) Notice: Subject to any disclaimer, the term of this patent is extended or adjusted under 35 U.S.C. 154(b) by 1007 days.

(21) Appl. No.: 10/538,994

(22) PCT Filed: Dec. 17, 2003

(86) PCT No.: PCT/NZ03/00280

§ 371 (c)(1),
(2), (4) Date: May 4, 2006

(87) PCT Pub. No.: WO2004/054766

PCT Pub. Date: Jul. 1, 2004

(65) Prior Publication Data

US 2006/0252847 A1    Nov. 9, 2006

(30) Foreign Application Priority Data

Dec. 18, 2002   (NZ) .................... 523237

(51) Int. Cl.
*A01N 43/707* (2006.01)
*B32B 21/00* (2006.01)
*C09K 5/16* (2006.01)

(52) U.S. Cl. ............... 427/255.25; 427/255.24; 427/303; 427/317; 523/122; 514/383; 428/292.2; 252/390

(58) Field of Classification Search ............ 428/292.4; 514/383; 523/122
See application file for complete search history.

(56) References Cited

U.S. PATENT DOCUMENTS

| 5,200,421 | A | * | 4/1993 | Ludwig et al. | 514/383 |
| 5,804,591 | A | * | 9/1998 | Valcke et al. | 514/383 |
| 5,874,025 | A | * | 2/1999 | Heuer et al. | 252/383 |
| 5,990,143 | A | * | 11/1999 | Ludwig et al. | 514/383 |
| 6,436,976 | B1 | * | 8/2002 | Erdelen et al. | 514/365 |
| 2002/0004517 | A1 | * | 1/2002 | Heuer et al. | 514/383 |
| 2004/0138217 | A1 | * | 7/2004 | Bruns et al. | 514/235.8 |
| 2004/0248973 | A1 | * | 12/2004 | Ross et al. | 514/483 |
| 2004/0258768 | A1 | * | 12/2004 | Richardson et al. | 424/630 |
| 2005/0233138 | A1 | | 10/2005 | Jobic | |
| 2008/0293793 | A1 | * | 11/2008 | Bruns et al. | 514/383 |

FOREIGN PATENT DOCUMENTS

| DE | 19648888 | 5/1998 |
| EP | 533016 | 3/1993 |
| EP | DE4320496 | 12/1994 |
| WO | WO 00/71314 | 11/2000 |

OTHER PUBLICATIONS

Beal, R.H.; "Preventing termite attack by adding insecticide to particleboard, hardboard, and plywood adhesive;" *Chemical Abstracts + Indexes, American Chemical Society*, vol. 11, No. 92, Mar. 17, 1980.

* cited by examiner

*Primary Examiner*—Joseph D Anthony
(74) *Attorney, Agent, or Firm*—Nicanor A. Kohncke

(57) ABSTRACT

The present invention relates to a method of using triadimefon and/or triadimenol as a preservative for the protection of glued wood-based products against attack and destruction of microorganisms, especially where the triadimefon and/or triadimenol is applied during the manufacturing process of the glued wood-based products. The invention further relates to a preservative composition for the protection of glued wood-based products including triadimefon and/or triadimenol and articles having such compositions as a part the article.

14 Claims, No Drawings

PRESERVATIVES FOR WOOD-BASED PRODUCTS

FIELD OF THE INVENTION

The present invention relates to antifungal preservatives for wood-based glued products.

BACKGROUND OF THE INVENTION

As a biological material, wood is subject to attack by fungi and insects. These organisms may damage the appearance of the wood, and they may seriously reduce it's structural strength. Wood and wood-based products can be protected from the effects of wood destroying organisms by applying fungicides or insecticides, or both. Such treatments can greatly improve the service life of the wood product, especially for timbers with low natural durability, such as radiata pine and other softwood species.

For some wood-based products, conventional methods of applying preservative treatment are inappropriate. For example, water based treatments such as copper chrome arsenate ("CCA") cannot be applied to laminated veneer products, particle based products or fibre based products without causing significant degrade and product loss. Other post-manufacture treatments for these products, such as light organic solvent preservative ("LOSP") are expensive and require a further processing step to achieve the treatment, creating extra cost.

A method favored by some wood-based product manufacturers is the application of a preservative by addition to the glue during manufacture. This approach can be used for any wood product that is constructed from relatively thin or small particles, such as wood fibre, wood chip or flake and thin wood veneer. Plywood, laminated veneer lumber (LVL), medium density fibreboard (MDF), waferboard/strandboard/oriented strandboard (OSB) and particleboard fall into this category.

The major drawbacks with this method of application lie in the nature of the glues used in the manufacturing process and the type of compounds available for treatment.

In general, glue systems for wood based products have high pH (9-12) or are highly reactive (e.g. isocyanate based glues). Thus the addition of a compound to such an environment can result in rapid degradation of the molecule. A further challenge to the robustness of the added compound is the curing condition for the glues. These are often high temperatures (~170° C.) in a high pressure pressing system.

These conditions require that any added preservative be robust enough to retain at least some of it's activity to be effective during the service life of the product.

It is known in the art that triazoles are generally effective against the *Basidiomycetes*, which are the fungi known to cause decay in wood. The triazoles most commonly used to protect solid wood from decay are tebuconazole and propiconazole. The amount of active ingredient needed in the wood to protect from decay has been shown to be in the order 50 g/m$^3$ wood to 300 g/m$^3$ wood for tebuconazole and 220 g/m$^3$ wood to 490 g/m$^3$ wood for propiconazole. It has also been disclosed that these two triazoles can act synergistically in some cases.

Furthermore, it is also known that due to the nature of the glue systems, the above mentioned triazoles that show activity in solid wood applications, when used in a glue-line treatment, have to be added in large quantities to the glue mixture due to subsequent breakdown in the process or due to inhomogeneous distribution in the wood based product.

A need therefore continues to exist for a preservative for wood-based products that can be applied in the manufacturing of wood-based products.

Applicant has surprisingly found that triadimefon and triadimenol can be used as preservatives for the protection of wood-based products against attack and destruction of microorganisms, especially of fungi.

Surprisingly triadimefon and triadimenol are stable under the conditions of the glue-line treatment and thus can be employed as preservatives in the manufacturing of glued wood-based products. In some cases, under alkaline conditions, triadimefon is being converted into triadimenol which is stable under these conditions and which also exhibits the required biological properties.

OBJECTS OF THE INVENTION

It is a first object of the present invention to provide a method of using triadimefon and/or triadimenol as an antimicrobial preservative for wood-based glued products.

It is a second object of the invention to provide a composition having improved antimicrobial properties as preservative for use in the production of wood-based glued products.

SUMMARY OF THE INVENTION

1. According to one aspect of the present invention there is provided method of using triadimefon and/or triadimenol as a preservative for the protection of glued wood-based products against attack and destruction of microorganisms characterized in that triadimefon and/or triadimenol is applied during the manufacturing process of the glued wood-based products.
2. According to a further aspect of the invention there is provided a composition for the protection of glued wood-based products against attack and destruction of microorganisms containing a glue, triadimefon and/or triadimenol.

MORE DETAILED DESCRIPTION OF THE INVENTION (±)1-(4-chlorophenoxy)-3,3-dimethyl-1-(1H-1,2,4-triazol-1-yl)butan-2-one (triadimefon) is a known triazole compound which is used in agriculture as a fungicide, especially for *Basidiomycete* control. Triadimefon has an alcohol analogue(±) 1-(4-chlorophenoxy)-3,3-dimethyl-1-(1H-1,2,4-triazol-1-yl)butan-2-ol (triadimenol), which shows similar activity and which is used for the same purpose. These known compounds are being superseded in agricultural uses by newer triazole compounds, such as propiconazole and tebuconazole, because of their higher activity at lower use rates.

TABLE 1

Agriculture use rates for selected triazoles.

| Active | Use rate range g/ha (agricultural uses)[1] |
| --- | --- |
| propiconazole | 100–150 |
| tebuconazole | 100–250 |
| triadimefon | 125–500 |
| triadimenol | 125–500 |

[1]Data from The Pesticide Manual, 12$^{th}$ Edition. British Crop Protection Council, Farnham, Surrey, UK. 2000

When the known triazoles are applied to wood based products as for example strandboard, particleboard, Medium Density Fibreboard (MDF), Plywood and Laminated Veneer Lumber (LVL) via the glueline, the expected levels of performance are not met at a said active content as would be expected.

Surprisingly, under these conditions, triadimefon and triadimenol show remarkable and consistent efficacy at surprisingly low levels. That means, improved levels of performance relative to the low amounts of triadimefon/triadimenol added are exhibited.

When used in the glue-line under alkaline conditions such as found in PF type glues, triadimefon may be reduced to the alcohol analogue triadimenol which surprisingly shows the same efficacy as triadimefon.

TABLE 2

Effective dosing rates for tebuconazole, propiconazole and triadimefon

| [1]Use rate gram a.i./m$^3$ | [2]Efficacy against target organism (expressed as weight loss percent in a standard rot trial with *Tyromyces palustris* as the target species)[1] | | |
|---|---|---|---|
| | Tebuconazole | Propiconazole | Triadimefon |
| 80 | 9.2 | — | — |
| 100 | — | 20.5 | 3.7 |
| 160 | 20.9 | — | — |
| 200 | — | 7.6 | 0.5 |
| 320 | 6.3 | — | — |
| 400 | — | 21.4 | 0.9 |
| 640 | 18.5 | — | — |
| 800 | — | 1.8 | 1.4 |
| Untreated | | 17.5 | |
| Commercial Standard [3]LOSP | | 5.8 | |

[1]In the glueline of plywood manufactured from *pinus* spp using phenol formaldehyde glue
[2]Using Japan Wood Preservers Association Standard Test procedure
[3]Light Organic Solvent Preservative (tributyl tin oxide)

The novel nature of this activity renders the triazole molecules triadimefon and triadimenol particularly suitable to the protection of glued wood based products from attack by microorganisms, especially of certain decay causing fungi.

According to the method of the present invention triadimefon and/or triadimenol are preferably added to the glue (glue-line treatment) during the manufacturing of glued wood-based products. Surprisingly according to the present invention triadimefon and/or triadimenol can be applied at low rates while a high protection of the wood-based products is provided.

The method of the present invention preferably provides protection of the glued wood-based products against attack and destruction of fungi.

Examples for wood destroying fungi are:
chaetomium as *chaetomium globosum* or
*chaetomium alba-arenulum*
*humicola grisea*
petriella as *petriella setifera*
trichurus as *trichurus spiralis*
*basidiomycetes*
coniophora as *coniophora puteana*
coriolus as *coriolus versicolor*
conkioporia as *donkioporia expans*
glenospora as *glenospora graphii*
gloeophyllum as *gloeophyllum abietinum* or
*gloeophyllum adoratum* or
*gloeophyllum protactum* or
*gloeophyllum sepiarium* or
*gloeophyllum trabeum*
lentinus as *lentinus cyathiformes* or
*lentinus edodes* or
*lentinus lepideus* or
*lentinus grinus* or
*Lentinus squarrolosus*
paxillus as *paxillus panuoides*
pleurotus as *pleurotus ostreatus*
poria as *poria monticola* or
*poria placenta* or
*poria vaillantii* or
*poria vaporaria*
serpula as *serpula himantoides* or
*serpula lacrymans*
stereum as *stereum hirsutum*
tyromyces as *tyromyces palustris*.

The process of manufacturing of glued wood-based products is in general commonly known. This process of manufacturing is generally used for any wood-composite product that is constructed from relatively thin or small particles, such as wood fibre, wood chip or flake and thin wood veneer. Plywood, laminated veneer lumber (LVL), medium density fibreboard (MDF), waferboard/strandboard/oriented strandboard (OSB) and particleboard can be manufactured by that method.

During this process the thin or small wood particles are combined with each other by addition of a glue or glue system under application of pressure to form a wood composite product. It is a known practice to add a wood preservative to the glue or glue system during the manufacturing process, the so-called glue-line treatment.

According to the method of the present invention, triadimefon and/or triadimenol are preferably added to the glue during the process of manufacturing of the wood-based products. It also possible to first prepare a composition containing a glue, triadimefon and/or triadimenol and optionally one or more solvents which are compatible with the glue or glue system and to apply such composition to the wood particles in the manufacturing process.

Solvents that can be used in the method of the present invention are for example N-methyl-pyrrolidone, glycolethers, texanole, benzyl alcohol, phenoxy ethanol, cyclohexanone.

High levels of glycols should be avoided because they might affect the viscosity or curing times of the glues.

Examples for the glue that can be used in the manufacturing of glued wood-based products are the following glues or glue systems: urea or urea phenol based systems as UF=urea-formaldehyde resins, PF=phenol-melamine(formaldehyde) resins, MUF=melamine(formaldehyde)-urea resins;
Polyvinyl alcohol (PVA) systems;
pMDI=polymeric methylene diphenyldiisocyanate.
Preferred are UF, MUF, PF and PVA systems.

In a further embodiment of the present invention triadimefon and/or triadimenol are used in mixture with at least one further fungicide, preferably selected from tebuconazole and cyproconazole.

It was found that surprisingly triadimefon and/or triadimenol enhance the protective effectiveness of other triazole fungicides, namely tebuconazole and cyproconazole, in glued wood based products, when applied in a combination product. Combinations of triadimefon with tebuconazole, preferably in a molar ratio of 5:1 to 1:2, or with cyproconazole, preferably in a molar ratio of 5:1 to 1:3, provide a broad protection of glued wood based products against decay causing fungi.

In a further embodiment of the present invention triadimefon and/or triadimenol are applied in combination with one or more insecticide that is known to be effective when applied via the glueline. Appropriate insecticides include synthetic pyrethroids—such as permethrin, cypermethrin, alpha-cypermethrin, deltamethrin, cyfluthrin, bifenthrin-, neo-nicotinoids—such as imidacloprid, clothianidin, acetamiprid, thiamethoxam-, chlorfenapyr, and fipronil. Mixtures of insecticides with triadimefon/triadimenol or combinations of triadimefon/triadimenol with tebuconazole or cyproconazole at appropriate rates will provide a simple one step application of preservative and gluing system for in-process treatment of most wood-based composites.

The present invention further provides a composition for the protection of glued wood-based products against attack and destruction of microorganisms. Such composition contains triadimefon and/or triadimenol and a glue or glue system. The preferred glues or glue systems are those mentioned above. The composition of the present invention may contain further additives such as solvents, which are compatible with the glue or glue system. The composition can alternatively be suspended in water such that the water becomes a component of the composition. The composition of the present invention can be prepared by commonly known methods, for example by mixing the single components. The composition can be used according to the method of the present invention by addition to the wood particles during the manufacturing process of wood-based glued products.

The invention claimed is:

1. A method of protecting a glued wood-based product comprising: applying a wood preservative consisting essentially of triadimefon and/or triadimenol, in combination with optional other further triazole fungicides, optional insecticides selected from the group consisting of synthetic pyrethroids, neonictinoids and mixtures thereof, and optional solvents, to an alkaline glue or glue system that is subsequently added to the glued wood-based product during the manufacturing thereof.

2. The method according to claim 1, wherein the wood-based product is formed from materials selected from the group consisting of wood fiber, wood chip, wood flake, thin wood veneer, plywood, laminated veneer lumber (LVL), medium density fiberboard (MDF), waferboard, strandboard, oriented strandboard (OSB), particleboard, and mixtures thereof.

3. The method according to claim 1, wherein the triadimefon and/or triadimenol are applied as a mixture with the alkaline glue or glue system.

4. The method according to claim 3, wherein the mixture of the alkaline glue or glue system and triadimefon and/or triadimenol is applied to the glued wood-based product by glue-line addition.

5. The method according to claim 3, wherein the mixture of the alkaline glue or glue system and triadimefon and/or triadimenol further comprises at least one further triazole fungicide.

6. The method according to claim 5, wherein the further triazole fungicide is tebuconazole, cyproconazole, or a mixture thereof.

7. The method according to claim 3, wherein the mixture of the alkaline glue or glue system and said triadimefon and/or triadimenol further comprises at least one further active insecticide selected from the group consisting of synthetic pyrethroids, neonictinoids and mixtures thereof.

8. The method according to claim 1, wherein said alkaline glue or glue system is selected from the group consisting of a urea based system, a urea-phenol based system, a phenol-melamine(formaldehyde)resin system, a melamine(formaldehyde-urea resin system; a polyvinyl alcohol based system; a polymeric methylene diphenyldiisocyanate system, and mixtures thereof.

9. A composition consisting essentially of: an alkaline glue or glue system, at least one triadimefon and/or triadimenol, optional further triazole fungicides, optional insecticides selected from the group consisting of synthetic pyrethroids, neonictinoids and mixtures thereof, and optional solvents.

10. The composition according to claim 9, further comprising at least one further active triazole fungicide or insecticide selected from the group consisting of synthetic pyrethroids, neonictinoids and mixtures thereof.

11. The composition according to claim 9, further comprising at least one solvent, said solvent being compatible with the alkaline glue or glue system or suspended or emulsified in water.

12. The composition according to claim 11, wherein said solvent is water.

13. The composition according to claim 9, wherein said alkaline glue or glue system is selected from the group consisting of a urea based system, a urea-phenol based system, a phenol-melamine(formaldehyde)resin system, a melamine(formaldehyde)-urea resin system; a polyvinyl alcohol based system; a polymeric methylene diphenyldiisocyanate system, and mixtures thereof.

14. An article comprising:
a glued wood-based product, said glued wood-based product comprising the composition according to claim 9.

* * * * *